(12) United States Patent
DeFalco et al.

(10) Patent No.: US 10,980,589 B2
(45) Date of Patent: *Apr. 20, 2021

(54) SCREW DRIVER, COMBINATION, AND RELATED METHODS

(71) Applicant: Zimmer Biomet Spine, Inc., Westminster, CO (US)

(72) Inventors: Anthony C. DeFalco, Lebanon, OH (US); Rawley Stanhope, Boonton, NJ (US); Daniel C. Taylor, Airmont, NY (US); Rui J. Ferreira, Livingston, NJ (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 63 days.

This patent is subject to a terminal disclaimer.

(21) Appl. No.: 16/359,534

(22) Filed: Mar. 20, 2019

(65) Prior Publication Data

US 2019/0216519 A1 Jul. 18, 2019

Related U.S. Application Data

(63) Continuation of application No. 15/390,895, filed on Dec. 27, 2016, now Pat. No. 10,258,403, which is a
(Continued)

(51) Int. Cl.
*A61B 17/88* (2006.01)
*A61B 17/70* (2006.01)
(Continued)

(52) U.S. Cl.
CPC ...... *A61B 17/8894* (2013.01); *A61B 17/7076* (2013.01); *A61B 17/7082* (2013.01);
(Continued)

(58) Field of Classification Search
CPC .............. A61B 17/808; A61B 17/8875; A61B 17/8894

See application file for complete search history.

(56) References Cited

U.S. PATENT DOCUMENTS

| 1,352,354 A | 9/1920 | Ira |
| 2,465,309 A | 3/1949 | Reynold et al. |

(Continued)

FOREIGN PATENT DOCUMENTS

| CN | 102858262 A | 1/2013 |
| CN | 104042320 A | 9/2014 |

(Continued)

OTHER PUBLICATIONS

"U.S. Appl. No. 13/799,791, Final Office Action dated Jan. 14, 2016", 8 pgs.
(Continued)

*Primary Examiner* — Nicholas W Woodall
(74) *Attorney, Agent, or Firm* — Schwegman Lundberg & Woessner, P.A.

(57) ABSTRACT

An orthopedic implant screw driver includes drive shaft. A first gear is operably coupled to the drive shaft and in meshing engagement with a hollow gear which rotates in response to rotation of the drive shaft. The hollow gear includes a passage defining an inwardly facing screw engagement periphery configured to receive and drivingly rotate a threaded portion of the screw. A method of securing an orthopedic implant to a bone includes positioning a screw within the passage which is configured to drivingly engage a threaded portion of the screw and rotating a drive shaft in driving engagement with the gear causing the gear to engage the screw along the threaded portion of the screw and rotatably drive the screw via the threaded portion.

16 Claims, 7 Drawing Sheets

Related U.S. Application Data continuation of application No. 13/799,791, filed on Mar. 13, 2013, now Pat. No. 9,539,043.

(51) Int. Cl.
  *A61F 2/46* (2006.01)
  *A61F 2/44* (2006.01)
  *A61B 17/00* (2006.01)

(52) U.S. Cl.
  CPC ........ *A61B 17/8875* (2013.01); *A61F 2/4455* (2013.01); *A61B 17/7074* (2013.01); *A61B 2017/00367* (2013.01)

(56) References Cited

U.S. PATENT DOCUMENTS

| | | | |
|---|---|---|---|
| 4,625,597 A | 12/1986 | Cast | |
| 4,636,217 A | 1/1987 | Ogilvie et al. | |
| 4,643,052 A | 2/1987 | Badiali | |
| 5,772,661 A | 6/1998 | Michelson | |
| 5,860,973 A | 1/1999 | Michelson | |
| 6,543,314 B1 | 4/2003 | Hoyt | |
| 6,723,126 B1 | 4/2004 | Berry | |
| 7,156,187 B1 | 1/2007 | Townsan | |
| 7,171,872 B1 | 2/2007 | Keusch | |
| 7,191,677 B2 | 3/2007 | Barkdoll | |
| 7,207,233 B2 | 4/2007 | Wadge | |
| 7,232,464 B2 | 6/2007 | Mathieu | |
| 7,674,296 B2 * | 3/2010 | Rhoda | A61F 2/44 623/17.15 |
| 7,704,279 B2 * | 4/2010 | Moskowitz | A61B 17/7064 623/17.11 |
| 7,708,779 B2 * | 5/2010 | Edie | A61F 2/44 623/17.15 |
| 7,814,816 B2 | 10/2010 | Alberti et al. | |
| 7,846,188 B2 | 12/2010 | Moskowitz et al. | |
| 7,862,616 B2 | 1/2011 | Lechmann et al. | |
| 7,875,076 B2 | 1/2011 | Mathieu et al. | |
| 8,172,854 B2 | 5/2012 | Blain et al. | |
| 8,282,683 B2 * | 10/2012 | McLaughlin | A61F 2/4455 623/17.11 |
| 9,539,043 B2 | 1/2017 | DeFalco et al. | |
| 9,615,866 B1 * | 4/2017 | Smith | A61B 17/8888 |
| 10,258,403 B2 | 4/2019 | DeFalco et al. | |
| 2006/0241621 A1 * | 10/2006 | Moskowitz | A61B 17/0642 623/17.11 |
| 2006/0293684 A1 | 12/2006 | Shluzas et al. | |
| 2007/0281274 A1 | 12/2007 | Schraffran et al. | |
| 2007/0282344 A1 | 12/2007 | Yedlicka et al. | |
| 2011/0087327 A1 | 4/2011 | Lechmann et al. | |
| 2011/0118843 A1 | 5/2011 | Mathieu et al. | |
| 2011/0160861 A1 * | 6/2011 | Jimenez | A61B 17/7065 623/17.16 |
| 2014/0276891 A1 | 9/2014 | Defalco et al. | |
| 2017/0172639 A1 | 6/2017 | Defalco et al. | |

FOREIGN PATENT DOCUMENTS

| | | |
|---|---|---|
| KR | 1020070108102 A | 11/2007 |
| WO | WO-2008042305 A2 | 4/2008 |

OTHER PUBLICATIONS

"U.S. Appl. No. 13/799,791, Non Final Office Action dated Jul. 30, 2015", 8 pgs.

"U.S. Appl. No. 13/799,791, Notice of Allowance dated Aug. 31, 2016", 5 pgs.

"U.S. Appl. No. 13/799,791, Response filed May 16, 2016 to Final Office Action dated Jan. 14, 2016", 7 pgs.

"U.S. Appl. No. 13/799,791, Response filed May 20, 2015 to Restriction Requirement dated Jan. 22, 2015", 3 pgs.

"U.S. Appl. No. 13/799,791, Response filed Sep. 29, 2015 to Non Final Office Action dated Jul. 30, 2015", 11 pgs.

"U.S. Appl. No. 13/799,791, Restriction Requirement dated Jan. 22, 2015", 6 pgs.

"U.S. Appl. No. 15/390,895, Non Final Office Action dated Jun. 29, 2018", 8 pgs.

"U.S. Appl. No. 15/390,895, Notice of Allowance dated Dec. 6, 2018", 5 pgs.

"U.S. Appl. No. 15/390,895, Preliminary Amendment filed Apr. 3, 2017", 7 pgs.

"U.S. Appl. No. 15/390,895, Response filed Oct. 1, 2018 to Non Final Office Action dated Jun. 29, 2018", 9 pgs.

"Chinese Application Serial No. 201410088438X, Office Action dated Nov. 9, 2015", 6 pgs.

\* cited by examiner

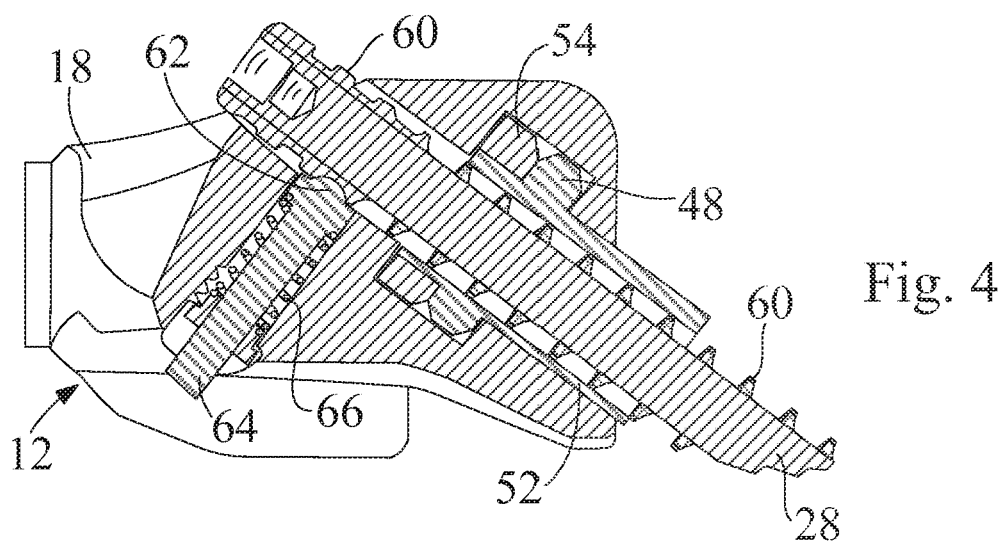
Fig. 4
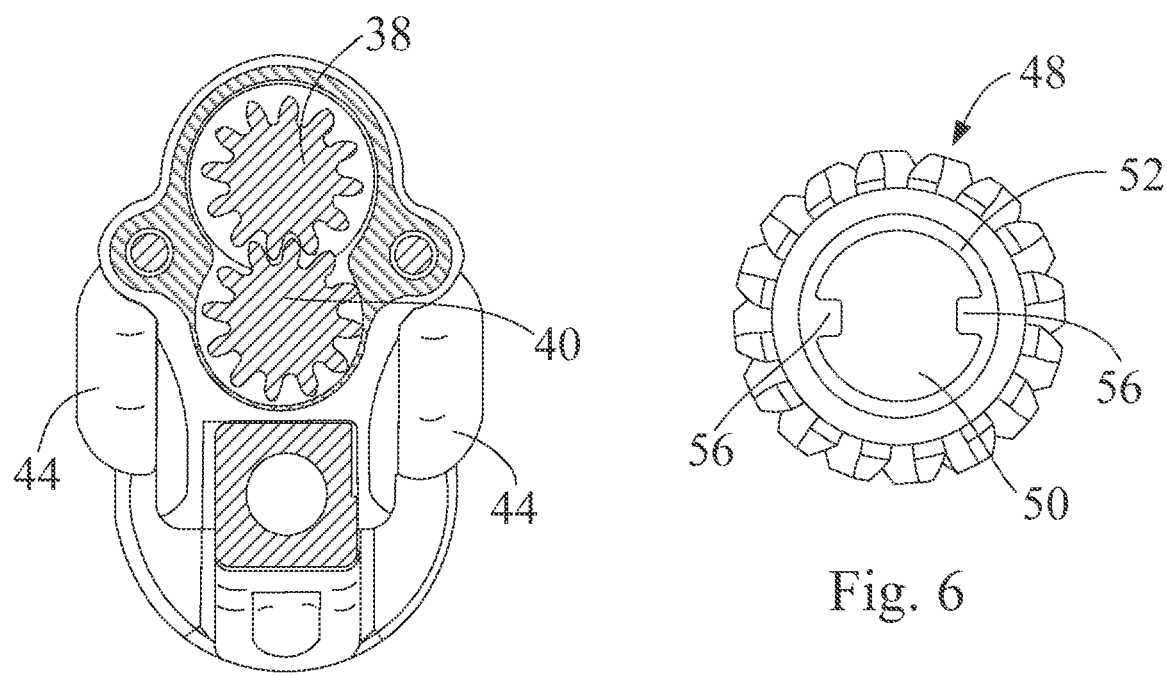
Fig. 5
Fig. 6

Fig. 6A
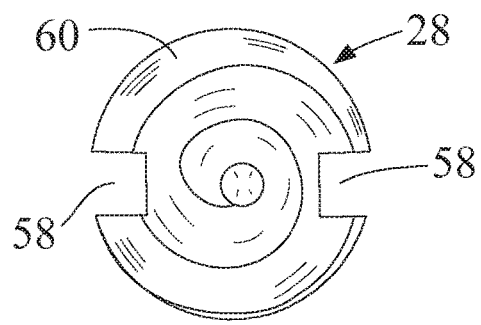
Fig. 6B
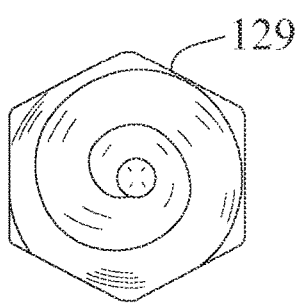
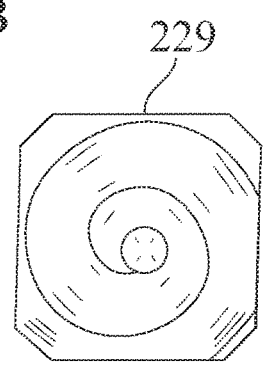
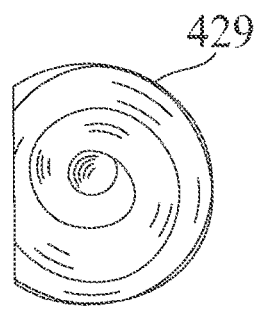
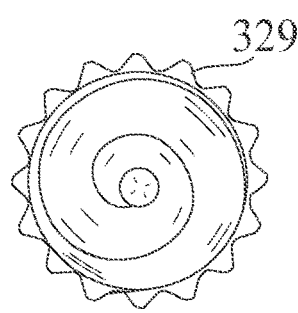
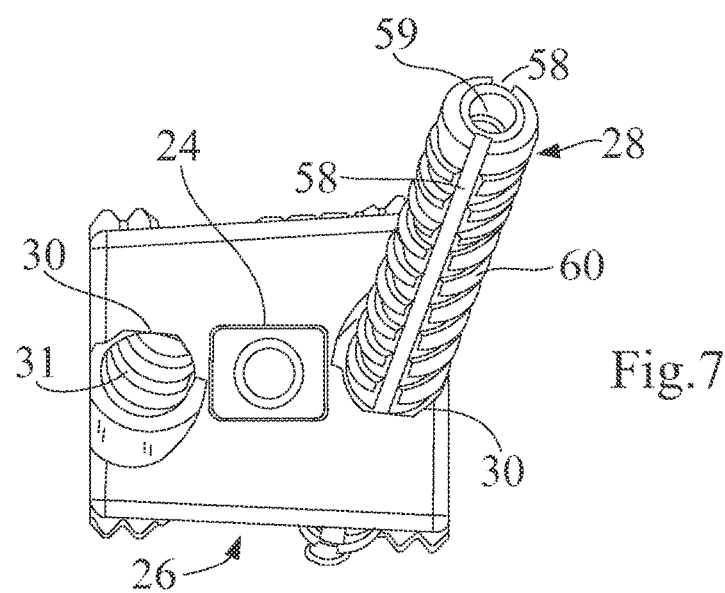
Fig. 7

SCREW DRIVER, COMBINATION, AND RELATED METHODS

FIELD

The present disclosure relates to screw driving implements and methods for driving a screw; and to such instruments and methods for securing a screw at angle during surgery.

BACKGROUND

This section provides background information related to the present disclosure which is not necessarily prior art.

The human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue or correct the deformity, which can require the use of one or more orthopedic prostheses, such as orthopedic screws, nails, etc.

In one example, in order to restore function to or correct a deformity of the spinal column, one or more intervertebral implants are used to restore the height and stabilize the anterior column of the spine. This technique can also be used through various lumbar approaches, such as anterior, posterior, posterolateral, direct lateral as well as through various approaches in the thoracic and cervical spinal regions. In some cases, additional stability and security of the spacer is achieved by affixing bone screws to the bone either exterior to the spacer, such as with pedicle screws and rods or anterior screws and plates, or through the spacer itself.

During surgery, for example, the angle or path of approach through an opening or channel in the body to the site where a screw needs to be attached can be very limited, both in direction and width. In some cases, the angle at which a screw needs to be driven can be quite different from the available angle of approach. In addition, it may be impossible or undesirable to widen the path or channel of approach or to create another opening through the body along the axis of the screw to allow a screw driver to engage the end of the screw. Driving screws at the desired angles and with the necessary torque is often difficult or impossible during surgery using standard screw drivers.

SUMMARY

This section provides a general summary of the disclosure, and is not a comprehensive disclosure of its full scope or all of its features.

In accordance with one particular aspect, the present teachings provide a screw driver for a surgical screw. The screw driver includes a housing and a drive shaft rotatably supported by the housing. A first gear is operably coupled to the drive shaft to rotate with the drive shaft. A second gear is rotatably supported by the housing in meshing engagement with the first gear to rotate in response to rotation of the first gear. The second gear includes a passage defining an inwardly facing screw engagement periphery configured to receive a threaded portion of the screw and, when positioned within the passage, to rotate the screw via engagement with a cooperating outwardly facing periphery defined by the threaded portion of the screw in response to rotation of the second gear.

In accordance with another particular aspect, the present teachings provide an angular screw driver for a surgical screw. The angular screw driver includes a drive shaft with a central shaft axis rotatably supported by a housing. A first gear is operably coupled to the drive shaft to rotate with the drive shaft. The first gear has an axis of rotation in alignment with the central shaft axis. A second gear is rotatably supported by the housing in meshing engagement with the first gear to rotate in response to rotation of the first gear. A through-passage extends through the screw driver including the second gear. The through-passage defines an inwardly facing periphery configured to drivingly rotate the screw. The through passage has a central passage axis that, is disposed at an angle relative to the central shaft axis. Rotation of the drive shaft rotates the first and second gears and, when the screw is positioned within the through-passage, rotates the screw through driving engagement of the inwardly facing screw engagement periphery of the through-passage with the cooperating outwardly facing periphery of the threaded portion of the screw.

In accordance with still yet another particular aspect, the present teachings provide a method of securing an orthopedic implant to a bone. The method includes positioning a screw within a central passage of a gear configured to drivingly engage a threaded portion of the screw and rotating a drive shaft in driving engagement with the gear causing the gear to engage the screw along the threaded portion of the screw and rotatably drive the screw via the threaded portion.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is a cross-sectional view taken through a portion of the distal end of the apparatus of FIG. 1.

FIG. 5 is a cross-sectional view taken along the line 5-5 of FIG. 1.

FIG. 6 is an end view showing an inwardly facing peripheral shape of a hollow driven gear of the apparatus of FIG. 1.

FIG. 6A is an end view showing a cooperating outwardly facing peripheral shape of a screw.

FIG. 6B is an end view similar to FIG. 6A of alternative outwardly facing peripheral shapes of various screws.

FIG. 7 is a lateral end view of the orthopedic implant of FIG. 1, the implant shown operatively associated with a bone screw.

Corresponding reference numerals indicate corresponding parts throughout the several views of the drawings.

DETAILED DESCRIPTION

Figure 1:
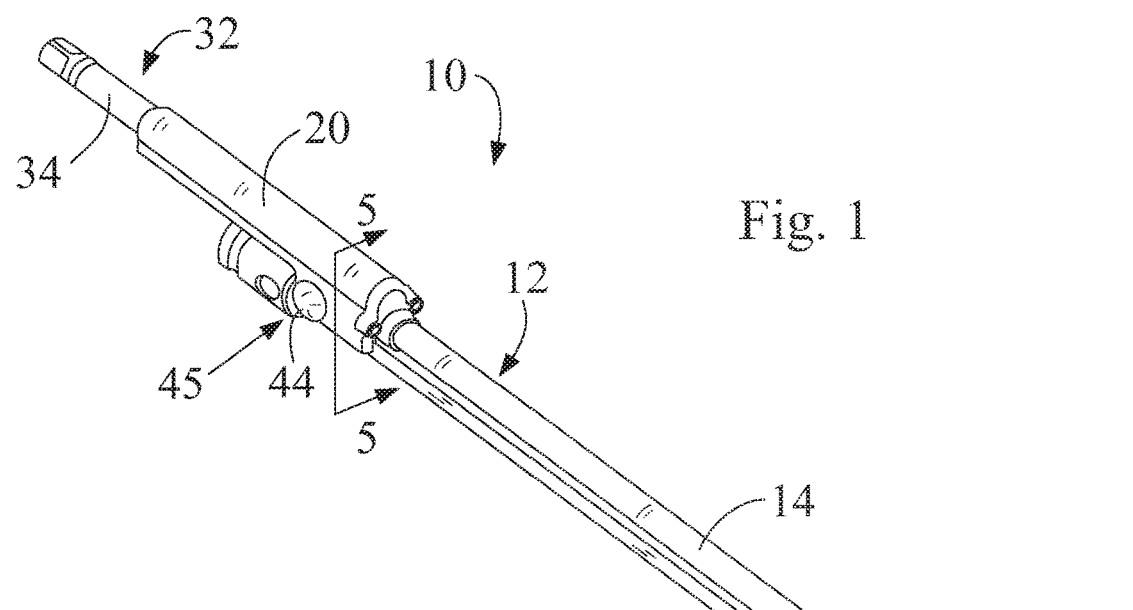
FIG. 1 is a perspective view of an apparatus for driving a screw constructed in accordance with the present teachings, the apparatus shown operatively associated with an orthopedic implant.
Figure 1A:
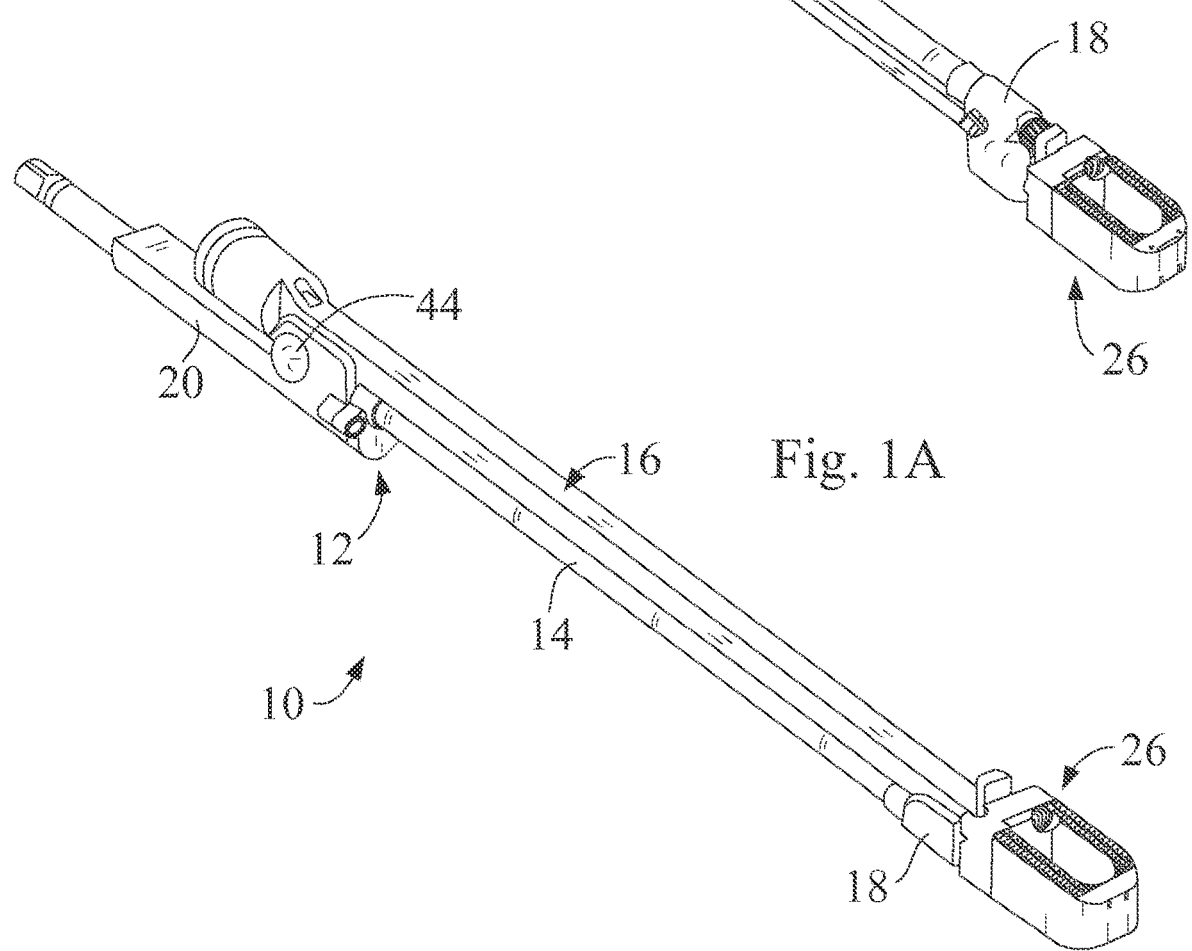
FIG. 1A is another perspective view of the apparatus of FIG. 1.

Example embodiments will now be described more fully with reference to the accompanying drawings. Although the screw driver is described and illustrated herein in the context of surgical procedures, including orthopedic screws and implants, those of ordinary skill in the art will appreciate that the screw driver disclosed herein, in its broadest aspects, has further applicability.

Referring to FIGS. 1 through 7, a screw driver apparatus 10 comprises a housing 12 including an elongated outer shaft 14 extending between a head member 18 and a terminal member 20. The various members of housing 12 can be separate components from each other or an be combined together with other housing members into a single component. The apparatus can be an orthopedic implant bone screw driver 10 used during surgery, and in such case, is sterile and manufactured of medical grade materials.

Figure 1B:
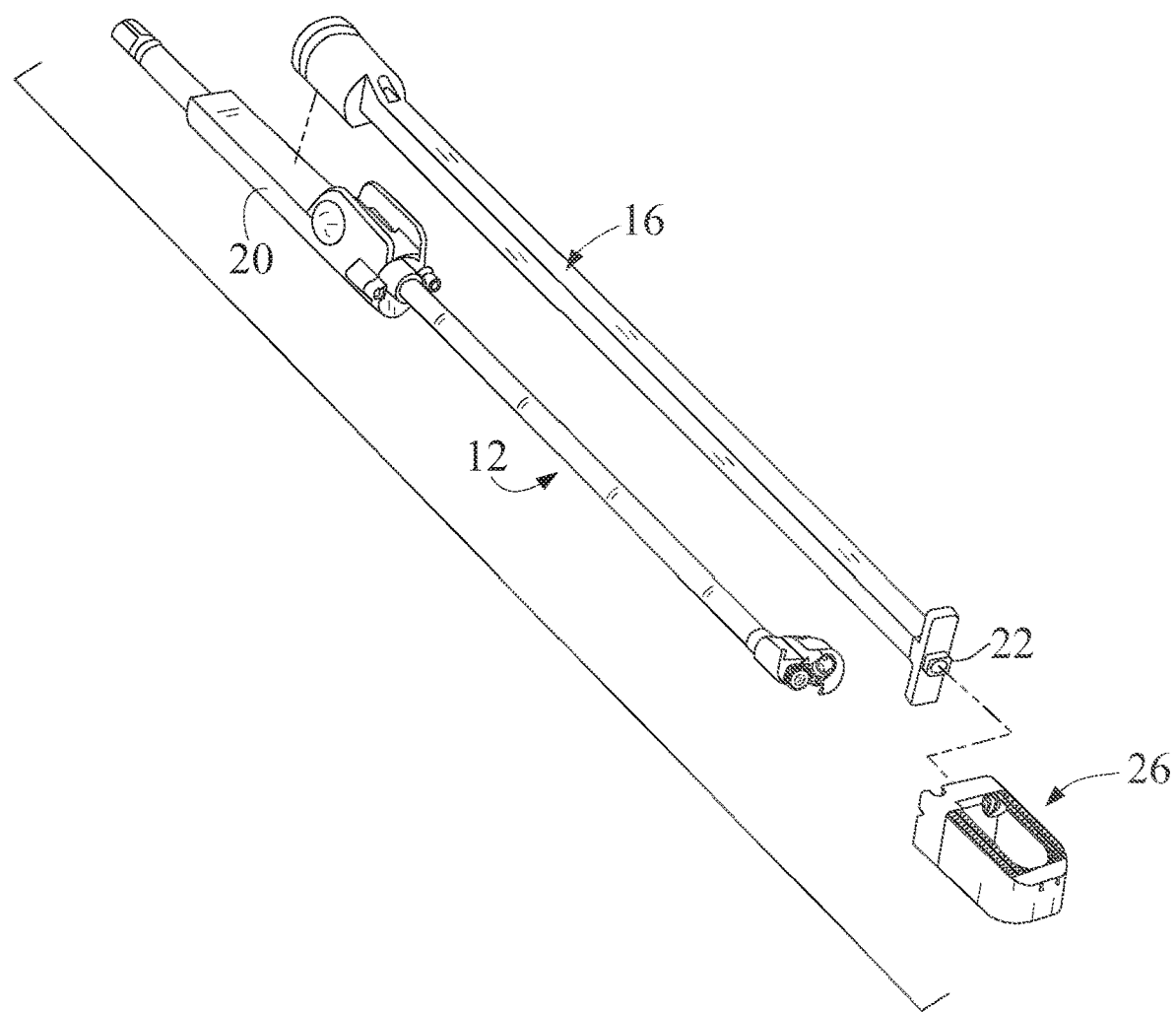
FIG. 1B is an exploded perspective view showing the screw driver separate from the implant and the implant positioner.
Figure 1C:
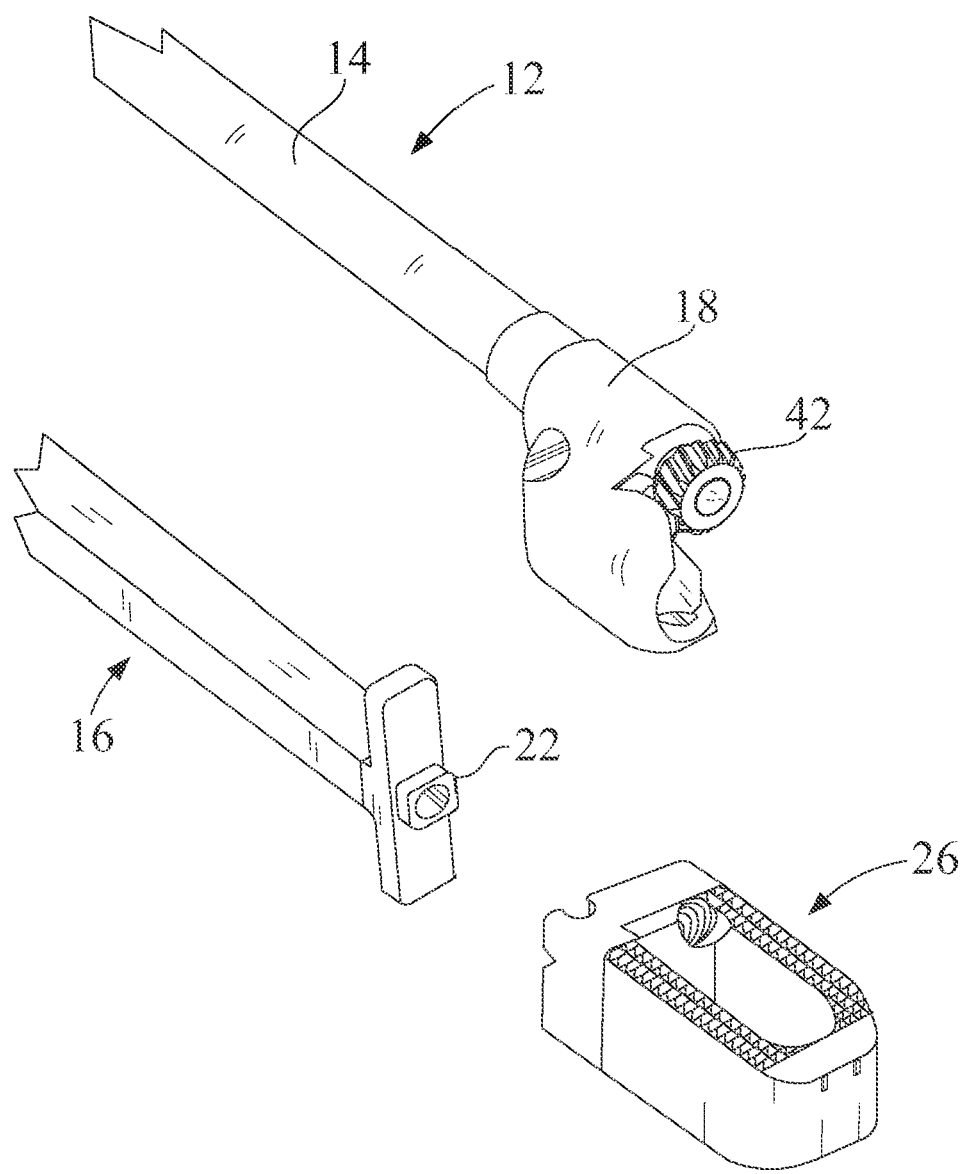
FIG. 1C is an enlarged partial perspective view of the distal end of the screw driver, the distal end of the implant positioner, and the implant.
Figure 2:
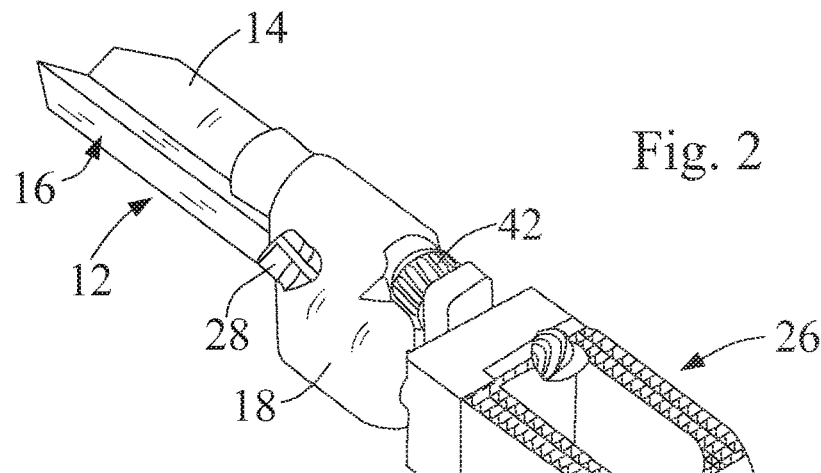
FIG. 2 is an enlarged perspective view of a distal end of the apparatus and orthopedic implant of FIG. 1.
Figure 3:
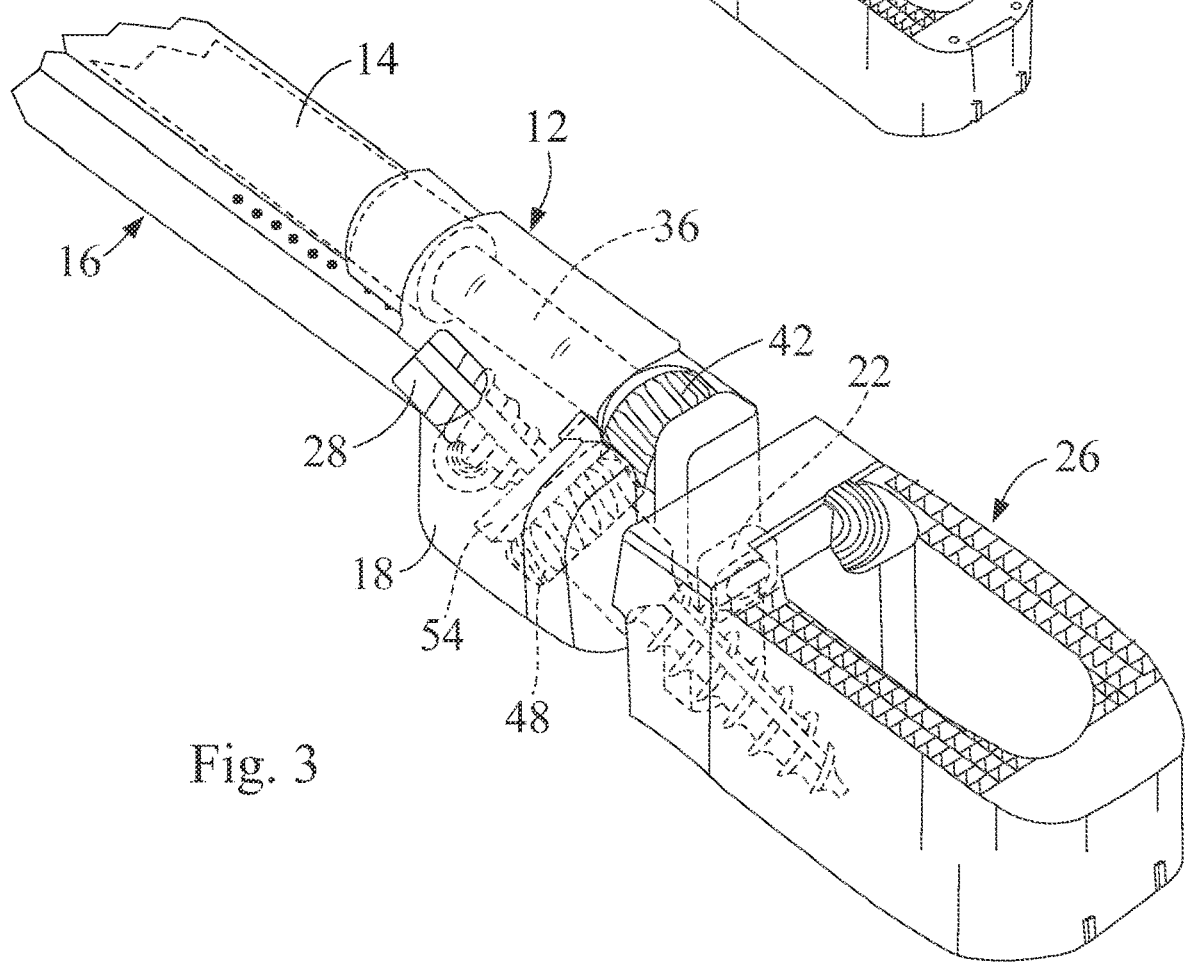
FIG. 3 is a further enlarged perspective similar to FIG. 2 with certain features interior to a gear housing in broken lines.
Figure 3A:
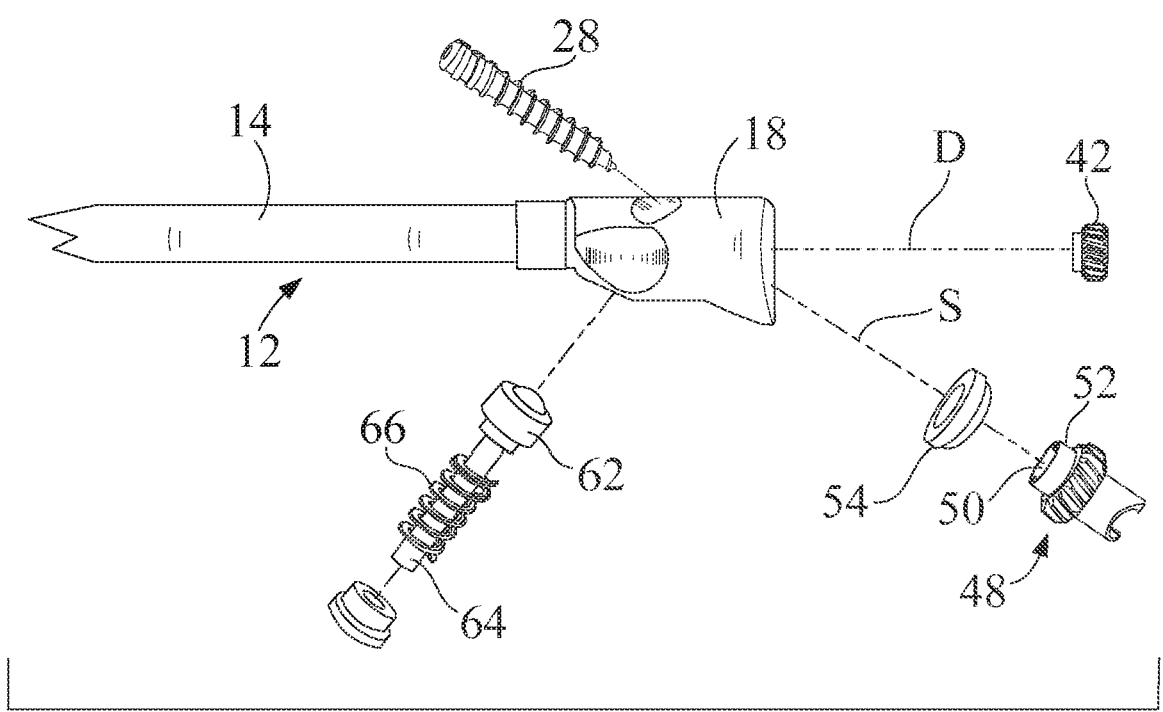
FIG. 3A is an exploded side view of the distal end of the screw driver illustrating its internal components, and the screw.

Screw driver 10 can be combined with an implant holder or positioner 16. Implant holder 16 can be releasable coupled to screw driver 10 by a locking mechanism 45 including a slidable thumb release 44. Implant holder 16 can include a positioning member 22 or protrusion (seen in FIGS. 1B and 1C) configured to engage with a cooperating positioning member 24 or recess (seen in FIG. 7) of an orthopedic implant 26 to align the two together in proper position. Such proper positioning of screw driver 10 relative to orthopedic implant 26 ensures that a screw 28 positioned within screw driver 10 is properly aligned with a corresponding threaded aperture 30 of the orthopedic implant. Thus, cooperating positioning members 22 and 24 are configured to engage each other in two positions, wherein each position aligns a screw 28 in screw driver 10 with one of two threaded apertures 30 within orthopedic implant 26. A first position is shown in FIGS. 2 and 3, for example. In a second position (not shown), the screw driver is rotated 180° about a longitudinal axis passing through the positioning member 22.

A drive shaft 32 comprises first shaft member 34 and second shaft member 36. First shaft member 34 has an end extending from a proximal side of housing 12 and carries a gear 38 (see FIG. 5) at a distal end thereof. Second shaft member 36 carries a gear 40 at one end and gear 42 at the other end. Gear 38 of first shaft member 34 is enmeshed with gear 40 of second shalt member 36. As a result, rotation of first shaft member 34 causes the second shaft member 36 to rotate in an opposite direction, which ultimately results in screw 28 rotating in the same direction as first shaft member 32 is rotated.

Gear 42 carried at distal end of shaft member 36 of drive shaft 32 is in meshing engagement with a hollow driven gear 8 that is rotatably supported by housing 12. Hollow driven gear 48 has a centrally located passage 50. Passage 50 can be open ended at both ends, thereby providing a through-passage. Through-passage 50 can extend not only through gear 48, but also through head 18 of housing 12. Through-passage 50 can allow a screw 28 to be inserted into screw driver 10 through the proximal end of through-passage 50, if desired.

Through-passage 50 can also allow the proximal end of a screw 28 within through-passage 50 to be uncovered, so that no part of screw driver 10 is positioned beyond the proximal end of screw 28 along the axis S of screw 28. Thus, the length of screw 28 can dictate the overall distance needed along the axis S of screw 28, minimizing the width of a path or channel of approach extending along the screw driver 10 axis D of drive shaft member 36.

Shaft member 36 of drive shaft 32 has an axis of rotation D provided by shaft member 36. Passage 50 of hollow driven gear 48 has a coincident axis of rotation S which is disposed at an angle relative to the drive shaft 32 axis D. Gear 48 comprises an axially extending cylindrical sleeve 52 partially defining passage 50. A bearing 54 is mounted around one end of cylindrical sleeve 52 helping to support gear 48 within housing 12.

Accordingly, the present teachings provide an orthopedic implant screw driver 10 in which screw 28 can be positioned within and held by driver 10. Thus, screw 28 can be delivered and positioned at the insertion sight along with orthopedic implant screw driver 10. Additionally, the orthopedic implant screw driver 10 allows screw 28 to be driven at angles that would otherwise be difficult or impossible using standard screw drivers, or which angles would require the use of larger incisions during surgery. In the illustrated example, an axis of rotation of passage 50 of hollow driven gear 48 (axis 5) is offset from and disposed at an angle relative to the axis of rotation of drive shaft 32 (axis D). Thus, axis D and axis S do not share a common plane, but an angle between axis S and axis D is between about 35 and about 45 degrees and can be about 40 degrees. It should be appreciated that other angles are possible, as is disposing axis D and axis S at an angle or parallel to each other so that they share a common plane.

Referring to FIG. 6, passage 50 has an inwardly facing peripheral shape defining a pair of opposing features or lug members 56. These lug members 56 can extend along the entire axial length of passage 50, or may extend only along a portion of its axial length. For example, lug members 56 may be positioned only at a distal or output end of passage 50.

Referring to FIG. 6A, screw 28 to be used in conjunction with screw driver 10 has an outwardly facing peripheral shape which corresponds inwardly facing peripheral shape of passage 50. Corresponding peripheral shape is provided along the threaded portion (which in this example includes the entire axial length) of screw 28 in the form of opposing elongated channels 58 interrupting screw thread 60. Thus, inwardly facing peripheral shape of passage 50 and outwardly facing peripheral shape of screw 28 are keyed or mated to each other. As a result, rotation of gear 48, including passage 50, drives rotation of screw 28 via threaded portion of screw 28.

Applying the rotational driving force to screw 28 along its side or periphery means that there is no need for anything to be provided beyond the proximal end of the screw 28 extending along the screw axis S. Because there is nothing behind the proximal end of screw 28 can be driven at essentially any angle relative to the access path or channel without needing to widen the path to account for screw driver components extending beyond the proximal end of screw 28 along the screw axis S. Screw driver 10 is also able to drive screws 28 at essentially any desired angle relative to the access path or channel without the need to apply axial pressure to the proximal end of screw 28.

FIG. 6B illustrates alternative peripheral shapes for a screw that passage 50 of hollow gear 48 may be configured to drive. As examples, a screw and corresponding passage of a screw driver hollow gear may have hexagonal 129, square 229, star 329, truncated circular 429 and other suitable corresponding peripheral shapes. Accordingly, it should be appreciated that the screw thread need not be interrupted by the outwardly facing peripheral shape of a screw.

Screw 28 includes a thread 60 that has a first pitch at its distal or insertion end. Thread 60 can have a second pitch at the proximal or trailing end of screw 28. As one possible example, this first pitch may extend about two-thirds the length of screw 28 where it transitions to the second pitch for about the remaining one-third of the axial length of screw 28. For example, first thread pitch may be about 2.4 mm and the second thread pitch may be about 2.3 mm.

Thread 60 of screw 28 also has a first thread type at its distal or insertion end. Thread 60 can have a second thread type at the proximal end of screw 28. As one possible example, a first pointed and/or thin thread type may extend about two-thirds the length of screw 28 where it transitions to the second squared and/or thick thread type for about the remaining one-third of the axial length of screw 28.

Screw 28 also has a first minor diameter (of the shaft) and a first major diameter (of the thread) at its distal end. Screw 28 can have a second major and/or minor diameter at the proximal end of screw 28. As one possible example, screw 28 has a major and minor diameter that may extend about two-thirds the length of screw 28 where one of both of the major and minor diameters begin gradually increasing along the remaining one-third of the axial length of screw 28. Thus, each of the pitch, thread type, and minor and major diameters are potentially variable dimensional characteristics of the threaded portion of screw 28.

Threaded apertures 30 of implant 26 may have a thread 31 with thread pitch that matches the first dimensional characteristic (e.g., thread pitch, type, major and minor diameters, and combinations thereof) of screw 28. Thus, as screw 28 is driven into threaded aperture 30 of implant 26, the second dimensional characteristic (e.g., thread pitch, type, major and minor diameters, and combinations thereof) of screw 28 begins to bind with the thread of implant 26. This creates a situation where screw 28 becomes effectively locked to implant 26 when screw 28 is torqued to the desired level, thereby reducing the possibility of screw 28 backing out after surgery. Although the above example, relates to changes along the threaded portion of screw 28 with the corresponding threaded aperture 30 of implant 26 being constant, the opposite configuration where thread 31 of aperture 30 change, or a configuration where both screw 28 and aperture 30 threads 31 and 60 change to provide a locking effect are contemplated.

Head member 18 of housing 12 of screw driver 10 may also include a timing feature in the form of a thread engaging member 62. The thread engaging member 62 rides in the space between two adjacent portions of thread 60 causing screw 28 to advance axially as it rotates relative to housing 12 until screw 28 may engage a threaded aperture 30 of implant 26.

An awl (not shown) may also be inserted into central passage 50 of screw driver 10 to provide a bore hole into the bone and then removed prior to using screw driver 10 to drive screw 28 through implant 26 and into the bone. For example, thread engaging member 62 can ride in a spiral recess of an awl that also has a cooperating outer peripheral shape. For example, thread engaging member 62 can ride in such a spiral recess to advance while lug members 56 of inwardly facing peripheral shape of passage 50 rotate the awl via engagement with cooperating outer peripheral shape.

As illustrated, thread engaging member 62 may be biased against thread 60 and manually movable away from screw thread by grasping and pulling extending pin 64 of thread engaging member 62 outwardly. Alternatively, a biasing member 66 may provide a biasing force which allows a user to simply push screw threads 60 past movable thread engaging member 62. In another alternative, thread engagement member 62 may be manually movable into an engaged position or a non-engaged position without the use of any biasing member. It may even be possible to provide thread engagement member 62 in a fixed position. Thus thread engagement member may allow a user to insert or remove a screw 28 from passage 50 without needing to rotate screw 28 relative to housing 12 or relative to gear 48, including central passage 50.

Applicable methods of using screw driver 10 should be apparent from the above discussion. Briefly, screw 28 is inserted into a first end of passage 50 with its rotational axis in alignment with the rotational axis of passage 50. During insertion, outward peripheral shape of screw 28 becomes rotationally aligned with the cooperating inward peripheral shape of passage 50 so that they engage each other.

During insertion, a thread engaging member 62 can become engaged with thread 60 of screw 28. In this case, thread engaging member 62 can move away from thread 60 of screw 28 during insertion in passage 50. For example, a user can manually pull threading engagement member 62 away using extending pin 64 or other means of displacing screw engaging member 62 away from thread 60 of screw 28. Alternatively, thread 60 can simply push threading engagement member 62 against biasing member 66 until it moves allowing thread 60 to pass.

After implant 26 is positioned adjacent the bone, screw driver 10 is properly positioned adjacent hole 30 by engaging positioning members 22 and 24 together. A user then rotates drive shaft 32 which drives gear 42 and driven hollow gear 48. Rotating drive shaft 32 causes gear 48 to engage screw 28 along the threaded portion of screw 28 and rotatably drive screw 28 via its threaded portion. Rotation of screw 28 against thread engaging member 62 drives the screw axially forward.

Thread 60 of screw 28 engages thread 31 of adjacent threaded aperture 30 of implant 26. This engagement between threads 31 and 60 continues to drive screw 28 forward and into the bone. As the first thread pitch of thread 31 of implant 26 engage against second thread pitch portion of thread 60 of screw 28, the two begin to bind against each other. The user can continue rotating drive shaft 32 until a desired torque is achieved, resulting in screw 28 becoming rotationally (and axially) locked into place due to the binding effect between threads 31 and 60.

The user can then pull screw driver 10 away from implant 26 wherein screw exits the distal end of passage 50. Thus, screw 28 can be inserted into passage 50 at one end and exit passage 50 at its opposite end. It is possible to sufficiently insert screw 28 into a final position within implant 26 via the cooperating peripheral shapes of passage 50 and screw 28. For example, only about one or two millimeters of screw 28 can extend from adjacent face of implant. Alternatively, a recess surrounding threaded aperture 30 can e distal end of cylindrical sleeve 52 to partially extend past adjacent face of implant 26 permitting the screw to be driven flush with such adjacent face.

Outward end of screw 28 can also be provided with a keyed aperture 59 which can be used to permit screw 28 to be removed, tightened, or otherwise repositioned. Keyed aperture 59 can be configured, for example, to mate with a Phillips screw driver, Allen wrench, star wrench, or other screw driving arrangement.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A screw driver for a surgical screw, comprising:
a housing;
a drive shaft rotatably supported by the housing;
a first gear operably coupled to the drive shaft to rotate with the drive shaft;
a second gear rotatably supported by the housing in meshing engagement with the first gear to rotate in response to rotation of the first gear, the second gear comprising a passage defining an inwardly facing screw engagement periphery configured to receive a threaded portion of the screw and, when positioned within the passage, to rotate the screw via engagement with a cooperating outwardly facing periphery defined by the threaded portion of the screw in response to rotation of the second gear; and
at least one engagement feature disposed in the passage for engaging a mating engagement feature along an axial length of at least a portion of the threaded portion of the screw.

2. The screw driver of claim 1, wherein the housing comprises a head member disposed at a distal end thereof, the head member defining a throughbore coincident with the passage of the second gear for receiving the screw, the throughbore including a timing feature for engaging the threaded portion of the screw in the passage causing the screw to axially advance when rotated relative to the housing.

3. The screw driver of claim 2, wherein the timing feature comprises a thread engaging member movably disposed in an opening disposed in the head member that is substantially perpendicular to and in communication with the throughbore.

4. The screw driver of claim 3, wherein the engaging member is biased towards the throughbore.

5. The screw driver of claim 1, wherein the at least one engagement feature disposed in the passage of the second gear comprises a lug and the mating engagement feature of the threaded portion of the screw comprises an elongated channel disposed therein.

6. The screw driver of claim 1, wherein the drive shaft has a drive shaft axis of rotation, and the passage has a passage axis of rotation which is disposed at a non-perpendicular angle relative to the drive shaft axis of rotation.

7. The screw driver of claim 1, further comprising an implant positioning member releasably coupled to at least a proximal end of the housing.

8. The screw driver of claim 1, wherein a distal end of the housing comprises an engagement member configured to mate with a cooperating engagement member or surgical implant to properly position the screw driver relative to the surgical implant.

9. An instrument for driving a surgical screw at a set angle relative to an implant, the instrument comprising:
a first gear disposed within a housing and coupled to a distal end of a drive shaft;
a hollow driven gear disposed within the housing in meshing engagement with the first gear, the hollow driven gear including an axially extending cylindrical sleeve at least partially defining a central passage configured to receive the surgical screw, at least a portion of the central passage including a screw mating feature to drive rotation of the surgical screw upon rotation of the hollow driven gear; and
a thread engaging member disposed adjacent to the central passage and configured to engage a threaded portion of the surgical screw to cause advancement of the surgical screw within the central passage upon rotation of the surgical screw by the hollow driven gear
wherein the drive shaft has a drive shaft axis of rotation, and the central passage has a passage axis of rotation which is disposed at an angle relative to the drive shaft axis of rotation, and wherein the angle is a non-perpendicular angle.

10. The instrument of claim 9, wherein the screw mating feature disposed in the central passage of the hollow driven gear comprises a lug configured to engage an elongated channel disposed along a length of the surgical screw.

11. The instrument of claim 9, wherein the thread engaging member is biased towards the central passage.

12. A method for inserting a surgical screw into an implant along a set angle, the method comprising:
inserting the surgical screw through a first end of a central passage, the central passage formed in part by a cylindrical driven gear configured to rotatably engage a portion of the surgical screw;
aligning an axis of rotation of the surgical screw within the central passage in a first direction which is disposed at a non-perpendicular angle to an axis of rotation of a drive shaft;
rotating the drive shaft in driving engagement with the hollow driven gear imparting rotation on the surgical screw which causes the surgical screw to linearly advance within the central passage; and
engaging the surgical screw within a threaded aperture of an orthopedic implant which pulls the surgical screw forward during rotation of the surgical screw.

13. The method of claim 12, wherein rotating the surgical screw within the central passage comprises rotating the surgical screw relative to a thread engaging member of a housing supporting the hollow driven gear to linearly advance the surgical screw.

14. The method of claim 13, wherein the surgical screw comprises a thread including a first thread pitch portion and a second thread pitch portion different than the first thread pitch portion, and
wherein rotating the drive shaft comprises causing the second thread pitch portion of the bone screw to bind against the thread engaging member to linearly advance the surgical screw.

15. The method of claim 12, wherein aligning the surgical screw within the central passage comprises aligning an inwardly facing screw engagement periphery defined by a cylindrical passage within the hollow driven gear with a cooperating outwardly facing periphery defined by a threaded portion of the surgical screw.

16. The method of claim 12, wherein the central passage is a through passage, and wherein rotating the drive shaft results in the surgical screw passing through the central passage and exiting a distal end of the central passage into an implant.

\* \* \* \* \*

UNITED STATES PATENT AND TRADEMARK OFFICE
CERTIFICATE OF CORRECTION

PATENT NO. : 10,980,589 B2
APPLICATION NO. : 16/359534
DATED : April 20, 2021
INVENTOR(S) : DeFalco et al.

It is certified that error appears in the above-identified patent and that said Letters Patent is hereby corrected as shown below:

In the Claims

In Column 8, Line 3, in Claim 8, delete "or" and insert --on a-- therefor

In Column 8, Line 22, in Claim 9, delete "gear" and insert --gear,-- therefor

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*